United States Patent
Marx et al.

(10) Patent No.: US 6,916,636 B2
(45) Date of Patent: Jul. 12, 2005

(54) NUCLEOTIDE SEQUENCES WHICH CODE FOR THE OXYR GENE

(75) Inventors: Achim Marx, Bielefeld (DE); Mike Farwick, Bielefeld (DE); Thomas Hermann, Bielefeld (DE); Natalie Schischka, Bielefeld (DE); Brigitte Bathe, Salzkotten (DE)

(73) Assignee: Degussa AG, Duesseldorf (DE)

( * ) Notice: Subject to any disclaimer, the term of this patent is extended or adjusted under 35 U.S.C. 154(b) by 297 days.

(21) Appl. No.: 09/938,641

(22) Filed: Aug. 27, 2001

(65) Prior Publication Data

US 2002/0064839 A1 May 30, 2002

Related U.S. Application Data

(60) Provisional application No. 60/279,415, filed on Mar. 29, 2001.

(30) Foreign Application Priority Data

Aug. 26, 2000 (DE) .......................................... 100 42 052
Mar. 2, 2001 (DE) .......................................... 101 10 053

(51) Int. Cl.[7] ................................................. C12P 13/04
(52) U.S. Cl. ...................... 435/106; 435/115; 435/69.1; 435/320.1; 435/252.3; 435/252.32; 435/254.11; 435/325; 435/419; 536/23.1; 536/23.2; 536/23.7
(58) Field of Search .............................. 536/23.1, 23.2, 536/23.7, 24.32, 23.6; 435/320.1, 252.3, 252.32, 254.11, 325, 419, 69.1, 106, 115, 254.1

(56) References Cited

U.S. PATENT DOCUMENTS

2002/0197605 A1 * 12/2002 Nakagawa et al. ............ 435/6

FOREIGN PATENT DOCUMENTS

EP 1 108 790 6/2001

OTHER PUBLICATIONS

GenBank Accession No. AE001274. Leishmania major chromosome 1, complete sequence, May 19, 1998.*
"Mycobacterium Avium Alkyl Hydroxperoxidase C (AHPC) Gene, and OxyR Homolog Gene", Jun. 3, 1995 GenBank Accession No. U18263.
"Streptomyces Coelicolor A3 (2) AHPD, AHPC, and OxyR Genes", Nov. 9, 1999 GenBank Accession No. AF186371.
"Mycobaxterium Marinum AHPC and OxyR Genes", Sep. 9, 1998 GenBank Accession No. AF034861.
R. Kraemer, Journal of Biotechnology, vol. 45, No. 1, pps. 1–21," Genetic and Physiological Approaches for the Production of Amino", Feb. 12, 1996.
A. Loos, et al., Applied and Environmental Microbiology, vol. 67, No. 5, pps. 2310–2318, "Development and Validation of Corynebacterium DNA Microarrays" May 2001.

* cited by examiner

*Primary Examiner*—Kathleen Kerr
(74) *Attorney, Agent, or Firm*—Oblon, Spivak, McClelland, Maier & Neustadt, P.C.

(57) ABSTRACT

The invention relates to polynucleotides corresponding to the oxyR gene from *Corynebacterium glutamicum* and which encode a OxyR transcriptional regulator, methods of producing L-amino acids, and methods of screening for polynucleotides which encode proteins having OxyR transcriptional regulator activity.

22 Claims, 2 Drawing Sheets

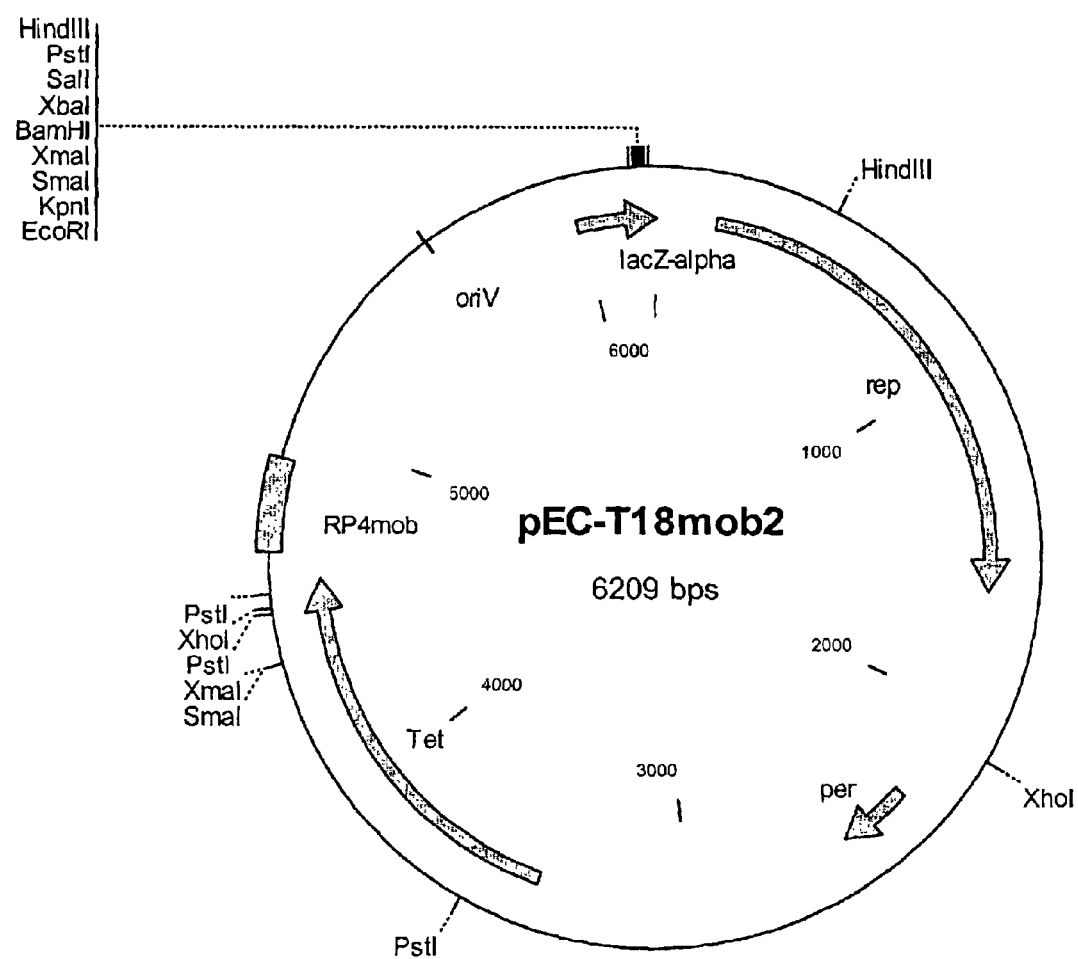
Figure 1: Map of the plasmid pEC-T18mob2

Figure 2: Map of the plasmid pT-oxyRexp
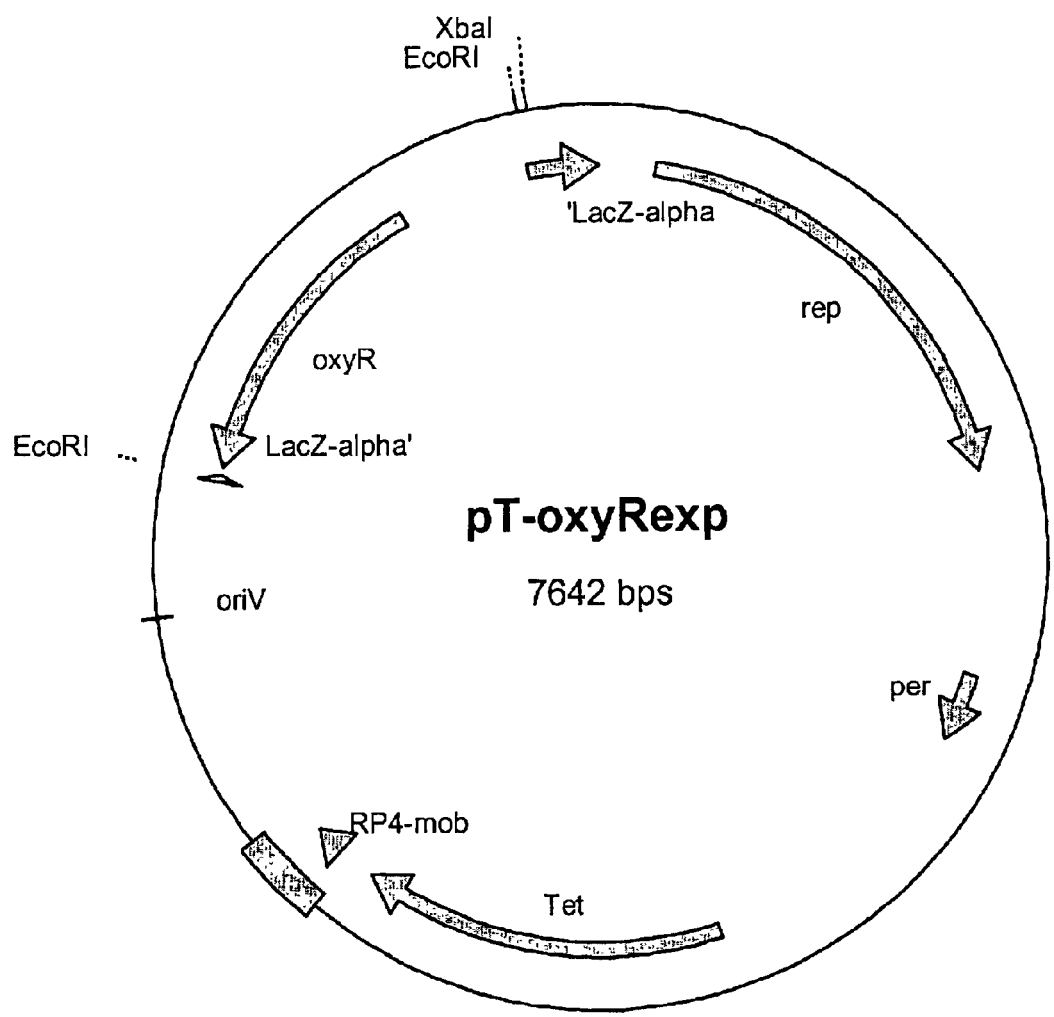

SEQUENCE LISTING

<160> NUMBER OF SEQ ID NOS: 4

<210> SEQ ID NO 1
<211> LENGTH: 1675
<212> TYPE: DNA
<213> ORGANISM: Corynebacterium glutamicum
<220> FEATURE:
<221> NAME/KEY: CDS
<222> LOCATION: (491)..(1471)
<223> OTHER INFORMATION:

<400> SEQUENCE: 1

```
gccaaccgca gggcatttac catcatggtg cgcaacgcca tgttccgcct tgtggagcta      60
tttgcttatg aaaaggaaga tcagcttagt cagatgactg aatacctgga tgaggctcct     120
gatttcggtg ctgcgatgga tgcgtacttt gatgaatatg cggatcttga taccggcccg     180
gcagctcgtg gaccagagtt cttcaaggta gagcacacgg gaagaatgtg ggaggtgcgt     240
caggtggtga aggatccaga aggtgataat tccttcgcgt ttgttgccac cattgatctt     300
gatgcctctg atgatgcagg tgaggtgcgt tttggatcgc tgtcgattga ccacaactag     360
gggtttgcgt cgaaaagcaa gcacgcctgg tgcctgattt gagcggtttt acctatggcg     420 cttttggcgcc gtcaaactgt cccagcgatt tcattattat tttcgtgcat tcaccgttat     480
agttataggc atg agc aat aaa gag tac cgg ccc aca ctc gcc cag ctt         529
           Met Ser Asn Lys Glu Tyr Arg Pro Thr Leu Ala Gln Leu
             1               5                  10 cgc acc ttt gtc acc atc gca gaa tgc aag cac ttt ggt act gct gcc        577
Arg Thr Phe Val Thr Ile Ala Glu Cys Lys His Phe Gly Thr Ala Ala
     15                  20                  25 acc aag ctg tcc att tcg cag cca tcc ctc tcc cag gca ctt gtc gca        625
Thr Lys Leu Ser Ile Ser Gln Pro Ser Leu Ser Gln Ala Leu Val Ala
 30                  35                  40                  45 tta gaa aca ggc ctg gga gtt cag ctg att gaa cgc tcc acc cgc aag        673
Leu Glu Thr Gly Leu Gly Val Gln Leu Ile Glu Arg Ser Thr Arg Lys
```

-continued

```
                50                  55                  60
gtc att gtc acc cca gcg ggc gag aag ttg ctg cca ttc gcc aaa tcc    721
Val Ile Val Thr Pro Ala Gly Glu Lys Leu Leu Pro Phe Ala Lys Ser
                65                  70                  75 acc ctt gac gcg gcg gag tct ttc ctc tcc cac gcc aag ggc gcc aac    769
Thr Leu Asp Ala Ala Glu Ser Phe Leu Ser His Ala Lys Gly Ala Asn
                80                  85                  90 ggt tcg ctc act gga ccg ttg acc gta ggc atc atc ccc acg gcg gct    817
Gly Ser Leu Thr Gly Pro Leu Thr Val Gly Ile Ile Pro Thr Ala Ala
        95                 100                 105 cct tac att ttg ccg tca atg ctg tcc atc gtg gat gaa gaa tat cca    865
Pro Tyr Ile Leu Pro Ser Met Leu Ser Ile Val Asp Glu Glu Tyr Pro
110                 115                 120                 125 gat ctg gaa cct cac atc gtc gag gac caa acc aag cat ctt ctc gcg    913
Asp Leu Glu Pro His Ile Val Glu Asp Gln Thr Lys His Leu Leu Ala
                130                 135                 140 ttg ctg cgc gac ggc gcc atc gac gtc gcc atg atg gcc ctg cct tct    961
Leu Leu Arg Asp Gly Ala Ile Asp Val Ala Met Met Ala Leu Pro Ser
                145                 150                 155 gag gca cca ggc atg aag gaa atc ccc ctc tac gac gaa gac ttt atc   1009
Glu Ala Pro Gly Met Lys Glu Ile Pro Leu Tyr Asp Glu Asp Phe Ile
                160                 165                 170 gtc gtt aca gct agc gat cac ccc ttc gcc ggc cgc caa gac tta gaa   1057
Val Val Thr Ala Ser Asp His Pro Phe Ala Gly Arg Gln Asp Leu Glu
        175                 180                 185 cta tcc gcc tta gaa gac ctc gat ctg ctg ctt ctc gac gac gga cac   1105
Leu Ser Ala Leu Glu Asp Leu Asp Leu Leu Leu Leu Asp Asp Gly His
190                 195                 200                 205 tgc ctc cac gac caa att gtg gac ctg tgc cgc cgc gga gac atc aac   1153
Cys Leu His Asp Gln Ile Val Asp Leu Cys Arg Arg Gly Asp Ile Asn
                210                 215                 220 ccc att agc tcc act act gct gtc acc cgc gca tcc agc ctt acc acc   1201
Pro Ile Ser Ser Thr Thr Ala Val Thr Arg Ala Ser Ser Leu Thr Thr
                225                 230                 235 gtc atg cag ctc gtc gtc gcc ggc ctt gga tcc acc ttg gtc cca atc   1249
Val Met Gln Leu Val Val Ala Gly Leu Gly Ser Thr Leu Val Pro Ile
                240                 245                 250 agc gca atc cca tgg gaa tgc acc cga cca gga ctg gca aca gcc aac   1297
Ser Ala Ile Pro Trp Glu Cys Thr Arg Pro Gly Leu Ala Thr Ala Asn
        255                 260                 265 ttc aac tct gat gtc acc gca aac cgc cgc att gga ttg gtg tac cgt   1345
Phe Asn Ser Asp Val Thr Ala Asn Arg Arg Ile Gly Leu Val Tyr Arg
270                 275                 280                 285 tcc tct tct tct cgc gcc gaa gag ttc gaa cag ttt gca ctc att ttg   1393
Ser Ser Ser Ser Arg Ala Glu Glu Phe Glu Gln Phe Ala Leu Ile Leu
                290                 295                 300 cag cgc gct ttc caa gaa gcc gtc gcg ctt gct gcc tca act ggc atc   1441
Gln Arg Ala Phe Gln Glu Ala Val Ala Leu Ala Ala Ser Thr Gly Ile
                305                 310                 315 acc ttg aag caa aat gtc gcg gta gcg cag taagtttttc tagaggtttt    1491
Thr Leu Lys Gln Asn Val Ala Val Ala Gln
                320                 325 ccagagtcag ctacaagcaa aaagcccttt ccattgatgc acaccaacgt gagattcaag   1551
ggaaagggct ttattgattg cagaatgcct actgcattag cggcgctcca ccggaatatt   1611
tccaccactg atctggcggt aaatatgaac ggtagacagc atcattactg gcagcacgat   1671
gatc                                                               1675
```

<210> SEQ ID NO 2
<211> LENGTH: 327
<212> TYPE: PRT
<213> ORGANISM: Corynebacterium glutamicum

<400> SEQUENCE: 2

Met Ser Asn Lys Glu Tyr Arg Pro Thr Leu Ala Gln Leu Arg Thr Phe
1               5                   10                  15

Val Thr Ile Ala Glu Cys Lys His Phe Gly Thr Ala Ala Thr Lys Leu
            20                  25                  30

Ser Ile Ser Gln Pro Ser Leu Ser Gln Ala Leu Val Ala Leu Glu Thr
        35                  40                  45

Gly Leu Gly Val Gln Leu Ile Glu Arg Ser Thr Arg Lys Val Ile Val
    50                  55                  60

Thr Pro Ala Gly Glu Lys Leu Leu Pro Phe Ala Lys Ser Thr Leu Asp
65                  70                  75                  80

Ala Ala Glu Ser Phe Leu Ser His Ala Lys Gly Ala Asn Gly Ser Leu
                85                  90                  95

Thr Gly Pro Leu Thr Val Gly Ile Ile Pro Thr Ala Ala Pro Tyr Ile
            100                 105                 110

Leu Pro Ser Met Leu Ser Ile Val Asp Glu Glu Tyr Pro Asp Leu Glu
        115                 120                 125

Pro His Ile Val Glu Asp Gln Thr Lys His Leu Leu Ala Leu Leu Arg
    130                 135                 140

Asp Gly Ala Ile Asp Val Ala Met Met Ala Leu Pro Ser Glu Ala Pro
145                 150                 155                 160

Gly Met Lys Glu Ile Pro Leu Tyr Asp Glu Asp Phe Ile Val Val Thr
                165                 170                 175

Ala Ser Asp His Pro Phe Ala Gly Arg Gln Asp Leu Glu Leu Ser Ala
            180                 185                 190

Leu Glu Asp Leu Asp Leu Leu Leu Asp Asp Gly His Cys Leu His
        195                 200                 205

Asp Gln Ile Val Asp Leu Cys Arg Arg Gly Asp Ile Asn Pro Ile Ser
    210                 215                 220

Ser Thr Thr Ala Val Thr Arg Ala Ser Ser Leu Thr Thr Val Met Gln
225                 230                 235                 240

Leu Val Val Ala Gly Leu Gly Ser Thr Leu Val Pro Ile Ser Ala Ile
                245                 250                 255

Pro Trp Glu Cys Thr Arg Pro Gly Leu Ala Thr Ala Asn Phe Asn Ser
            260                 265                 270

Asp Val Thr Ala Asn Arg Arg Ile Gly Leu Val Tyr Arg Ser Ser Ser
        275                 280                 285

Ser Arg Ala Glu Glu Phe Glu Gln Phe Ala Leu Ile Leu Gln Arg Ala
    290                 295                 300

Phe Gln Glu Ala Val Ala Leu Ala Ala Ser Thr Gly Ile Thr Leu Lys
305                 310                 315                 320

Gln Asn Val Ala Val Ala Gln
                325

<210> SEQ ID NO 3
<211> LENGTH: 30
<212> TYPE: DNA
<213> ORGANISM: Artificial Sequence
<220> FEATURE:
<223> OTHER INFORMATION: Synthetic DNA

<400> SEQUENCE: 3

```
gatcgagaat tcaaaggaag atcagcttag                                         30

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
ggaaaacctc tagaaaaact                                                    20
```

NUCLEOTIDE SEQUENCES WHICH CODE FOR THE OXYR GENE

CROSS-REFERENCE TO RELATED APPLICATIONS

The present application claims priority to the U.S. provisional Application No. 60/279,415 filed Mar. 29, 2001, German Application No. DE 10110053.1 filed Mar. 2, 2001, and German Application No. DE 10042052.4 filed Aug. 26, 2000; the entire contents of all three applications are incorporated herein by reference.

BACKGROUND OF THE INVENTION

1. Field of the Invention

The invention provides nucleotide sequences from *Coryneform* bacteria which code for the oxyR gene and a process for the fermentative preparation of amino acids, in particular L-lysine, using bacteria in which the oxyR gene is enhanced. The oxyR gene codes for the transcription regulator OxyR, which belongs to the LysR family.

2. Discussion of the Background

L-Amino acids, particularly L-lysine, are used in human medicine and in the pharmaceuticals industry, in the foodstuffs industry and, most particularly in animal nutrition.

It is known that amino acids are prepared by fermentation from strains of *Coryneform* bacteria, in particular *Corynebacterium glutamicum*. Because of their great importance, attempts are constantly being made to improve the preparation processes. Improvements to the process may concern measures relating to fermentation, for example, stirring and oxygen supply, or the composition of the nutrient media, such as, the sugar concentration during the fermentation, or the working up to the product form by, for example, ion exchange chromatography, or the intrinsic output properties of the microorganism itself The output properties of these microorganisms are improved by employing methods of mutagenesis, selection, and mutant selection. These methods yield strains that produce amino acids, such as the lysine analogue S-(2-aminoethyl)-cysteine, and are resistant to antimetabolites or are auxotrophic for metabolites important for regulation. In this manner, L-lysine can be obtained from these strains.

For a number of years, methods of the recombinant DNA technology have also been used for improving L-amino acid-producing strains of *Corynebacterium*. However, there remains a critical need for improved methods of producing L-amino acids and thus for the provision of strains of bacteria producing higher amounts of L-amino acids. On a commercial or industrial scale even small improvements in the yield of L-amino acids, or the efficiency of their production, are economically significant. Prior to the present invention, it was not recognized that enhanced expression of the oxyR gene encoding the OxyR transcriptional regulator would improve L-amino acid yields.

SUMMARY OF THE INVENTION

An object of the present invention is to provide novel measures for the production of amino acids or L-amino acids, where these amino acids include L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine and the salts (monohydrochloride or sulfate) thereof.

One object of the present invention is providing a novel process for improving the fermentative production of said L-amino acids, particularly L-lysine. Such a process includes enhanced bacteria, preferably enhanced *Coryneform* bacteria, which express enhanced amounts of the OxyR transcriptional regulator, which is encoded by oxyR gene.

Thus, another object of the present invention is providing such a bacterium, which expresses an enhanced amount of OxyR transcriptional regulator or gene products of the oxyR gene.

Another object of the present invention is providing a bacterium, preferably a *Coryneform* bacterium, which expresses a polypeptide that has enhanced OxyR transcriptional regulator activity.

Another object of the invention is to provide a nucleotide sequence encoding a polypeptide which has OxyR transcriptional regulator protein sequence. One embodiment of such a sequence is the nucleotide sequence of SEQ ID NO:1.

A further object of the invention is a method of making OxyR transcriptional regulator or an isolated polypeptide having a OxyR transcriptional regulator activity, as well as use of such isolated polypeptides in the production of amino acids. One embodiment of such a polypeptide is the polypeptide having the amino acid sequence of SEQ ID NO:2.

Other objects of the invention include methods of detecting nucleic acid sequences homologous to SEQ ID NO:1, particularly nucleic acid sequences encoding polypeptides that have OxyR transcriptional regulator activity, and methods of making nucleic acids encoding such polypeptides.

The above objects highlight certain aspects of the invention. Additional objects, aspects and embodiments of the invention are found in the following detailed description of the invention.

BRIEF DESCRIPTION OF THE DRAWINGS

FIG. 1: Map of the plasmid pEC-T18mob2.

FIG. 2: Map of the plasmid pT-oxyRexp.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory, New York (1982) and Sambrook et al., Molecular Cloning: A Laboratory Manual, Cold Spring Harbor Laboratory, New York (1989) and the various references cited therein.

The invention provides an isolated polynucleotide from *Coryneform* bacteria, containing a polynucleotide sequence coding for the oxyR gene, selected from the group consisting of a) polynucleotide that is at least 70% identical to a polynucleotide that codes for a polypeptide containing the amino acid sequence of SEQ ID No. 2, b) polynucleotide that codes for a polypeptide containing an amino acid sequence that is at least 70% identical to the amino acid sequence of SEQ ID No. 2, c) polynucleotide that is complementary to the polynucleotides of a) or b), and d) polynucleotide containing at least 15 successive nucleotides of the polynucleotide sequence of a), b) or c), the polypeptide preferably having the activity of the transcription regulator OxyR.

The invention also provides the above-mentioned polynucleotide, preferably being a replicable DNA containing:

(i) the nucleotide sequence shown in SEQ ID No. 1, or (ii) at least one sequence that corresponds to sequence (i) within the range of degeneracy of the genetic code, or (iii) at least one sequence that hybridizes with the sequences that are complementary to sequence (i) or (ii), and optionally (iv) sense mutations in (i) that are neutral in terms of function.

The invention also provides:

polynucleotides containing at least 15 successive nucleotides chosen from the nucleotide sequence of SEQ ID No. 1 between positions 1 and 490;

polynucleotides containing at least 15 successive nucleotides chosen from the nucleotide sequence of SEQ ID No. 1 between positions 491 and 1471; and polynucleotides containing at least 15 successive nucleotides chosen from the nucleotide sequence of SEQ ID No. 1 between positions 1472 and 1675.

Additional provisions of this invention are:

a replicable DNA containing the nucleotide sequence as shown in SEQ ID No. 1;

a polynucleotide that codes for a polypeptide containing the amino acid sequence as shown in SEQ ID No. 2;

a vector containing the DNA sequence of *Corynebacterium glutamicum* which codes for the oxyR gene, deposited in *Corynebacterium glutamicum* as pT-oxyRexp under DSM 13457 at the DSMZ, Braunschweig (Germany);

and, *Coryneform* bacteria that contain the vector carrying the oxyR gene or in which the oxyR gene expression is enhanced.

The invention also provides polynucleotides consisting substantially of a polynucleotide sequence, which are obtainable by screening by means of hybridization, of a corresponding *Coryneform* gene library that contains the complete gene having the polynucleotide sequence according to SEQ ID No. 1 or parts thereof, using a probe containing the sequence of said polynucleotide according SEQ ID No. 1 or a fragment thereof, and isolating said polynucleotide sequence.

Polynucleotide sequences according to the invention are suitable as hybridization probes for RNA, cDNA and DNA, in order to isolate the full length nucleic acids or polynucleotides or genes that code for the transcription regulator OxyR, or in order to isolate nucleic acids or polynucleotides or genes that have a high similarity with the sequence of the oxyR gene. These polynucleotide sequences are also suitable for incorporation into arrays, micro-arrays or DNA-chips in order to detect and determine the corresponding polynucleotides.

The DNA of genes that code for the transcription regulator OxyR can be prepared with the polymerase chain reaction (PCR) by using polynucleotides according to the invention as primers.

Such oligonucleotides acting as probes or primers contain at least 25–30, preferably at least 20–24, more preferably at least 15–19 consecutive nucleotides. Also suitable are oligonucleotides that have a length of at least 31–40 or at least 41–50 nucleotides. Additional oligonucleotides that are suitable have a length of at least 100, 150, 200, 250 or 300 nucleotides.

"Isolated" means removed out of its natural environment.

"Polynucleotide" generally refers to polyribonucleotides and polydeoxyribonucleotides. The RNA or DNA may be modified or un-modified.

The polynucleotides according to the invention include a polynucleotide shown in SEQ ID No. 1 or a fragment prepared therefrom and also those that are at least 70% to 80%, preferably at least 81% to 85%, more preferably at least 86% to 90%, and most preferably at least 91% to 99% identical to the polynucleotide according to SEQ ID No. 1 or a fragment prepared therefrom.

"Polypeptides" are understood as being peptides or proteins that comprise two or more amino acids bonded via peptide bonds.

The polypeptides according to the invention include a polypeptide shown in SEQ ID No. 2, particularly those with the biological activity of the transcription regulator OxyR, and also those that are at least 70% to 80%, preferably at least 81% to 85%, more preferably at least 86% to 90%, and most preferably at least 91% to 99% identical to the polypeptide according to SEQ ID No. 2 and exhibit the mentioned activity.

The invention also provides a process for the production of amino acids, where these amino acids include L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine using *Coryneform* bacteria that, in particular, already produce amino acids and in which the nucleotide sequences coding for the oxyR gene are enhanced, in particular overexpressed.

The term "enhancement" in this connection describes the increase in the intracellular activity of one or more enzymes in a microorganism that are coded by the corresponding DNA, by, for example increasing the number of copies of the gene or genes, using a potent promoter, or using a gene or allele coding for a corresponding enzyme having a high activity, and optionally combining these measures.

The microorganisms provided by the present invention may prepare L-amino acids, in particular L-lysine, from glucose, sucrose, lactose, fructose, maltose, molasses, starch, cellulose or from glycerol and ethanol. The microorganisms may be representatives of *Coryneform* bacteria, in particular of the genus *Corynebacterium*. *Corynebacterium glutamicum* species of this genus garners special since it is well known to those skilled in the art for its ability to produce L-amino acids.

Suitable strains of the genus *Corynebacterium*, in particular of the species *Corynebacterium glutamicum* (*C. glutamicum*), are, in particular the known wild-type strains

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869, and
*Brevibacterium divaricatum* ATCC14020 or L-amino acid-producing mutants or strains prepared therefrom, for example, the L-lysine producing strains Corynebacterium glutamicum FERM-P 1709
Corynebacterium glutamicum FERM-P 6463
Corynebacterium glutamicum FERM-P 6464
Corynebacterium glutamicum DSM5715.
Brevibacterium flavum FERM-P 1708, and
Brevibacterium lactofermentum FERM-P 1712

Preferably, a bacterial strain with enhanced expression of a oxyR gene that encodes a polypeptide with transcription regulator OxyR activity will improve amino acid yield at least 1%.

The inventors have succeeded in isolating the new oxyR gene of *C. glutamicum* that codes for the transcription regulator OxyR.

To isolate the oxyR gene or also other genes of *C. glutamicum*, a gene library of that microorganism is prepared in *Escherichia coli* (*E. coli*). The preparation of gene libraries is described in generally known textbooks and handbooks. For example, the textbook of Winnacker: Gene and Klone, Eine Einführung in die Gentechnologie (Verlag Chemie, Weinheim, Germany, 1990) or the handbook by Sambrook et al.: Molecular Cloning, A Laboratory Manual (Cold Spring Harbor Laboratory Press, 1989). A well-known gene library is that of the *E. coli* K-12 strain W3110, which has been prepared by Kohara et al. (Cell 50, 495–508 (1987)) in λ vectors. Bathe et al. (Molecular and General Genetics, 252:255–265, 1996) describe a gene library of *C. glutamicum* ATCC13032, which was prepared with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575). Börnann et al. (Molecular Microbiology 6(3), 317–326) (1992)) in turn describe a gene library of *C. glutamicum* ATCC13032 using the cosmid pHC79 (Hohn and Collins, Gene 11, 291–298 (1980)).

It is possible to use plasmids such as pBR322 (Bolivar, Life Sciences, 25, 807–818 (1979)) or pUC9 (Viera et al., 1982, Gene, 19:259–268) in order to prepare a gene library of *C. glutamicum* in *E. coli*. Suitable hosts are particularly those *E. coli* strains, which are restriction- and recombination-deficient, such as the strain DH5αMCR, which has been described by Grant et al. (Proceedings of the National Academy of Sciences USA, 87 (1990) 4645–4649).

The long DNA fragments cloned with the aid of cosmids or other λ vectors can then be subcloned into the usual vectors suitable for sequencing as described inter alia by Sanger et al. (Proceedings of the National Academy of Sciences of the United States of America, 74:5463–5467, 1977).

The resulting DNA sequences can then be investigated with known algorithms or sequence analysis programs, such as that of Staden (Nucleic Acids Research 14, 217–232 (1986)),that of Marck (Nucleic Acids Research 16, 1829–1836 (1988)) or the GCG program of Butler (Methods of Biochemical Analysis 39, 74–97 (1998)).

In that manner, the novel DNA sequence of *C. glutamicum* that codes for the oxyR gene (SEQ ID No. 1) has been obtained and forms part of this invention. Furthermore, the amino acid sequence of the corresponding protein has been derived from the present DNA sequence by the methods described above. The resulting amino acid sequence of the oxyR gene product is shown in SEQ ID No. 2. It is known to those skilled in the art that enzymes endogenous in the host can remove the N-terminal amino acid methionine or formylmethionine, as such the resulting form of the transcription regulator OxyR forms part of this invention.

Coding DNA sequences that result from SEQ ID No. 1 by the degeneracy of the genetic code also form part of the invention. In the same way, DNA sequences that hybridize with SEQ ID No. 1 or parts of SEQ ID No. 1 form part of the invention. Furthermore, to a person skilled in the art, conservative amino acid exchanges, such as exchange of glycine for alanine or of aspartic acid for glutamic acid in proteins, are known as "sense mutations." These mutations do not lead to a fundamental change in the activity of the protein, i.e. are neutral in terms of function. It is also known that changes on the N and/or C terminus of a protein may not substantially impair or may even stabilize the function thereof. The person skilled in the art will find relevant information inter alia in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences that result in a corresponding manner from SEQ ID No. 2 also form part of the invention.

DNA sequences that hybridize with SEQ ID No. 1 or parts of SEQ ID No. 1 form part of the invention. Finally, DNA sequences that are prepared by the polymerase chain reaction (PCR) using primers that result from SEQ ID No. 1 form part of the invention. Such oligonucleotides typically have a length of at least 15 nucleotides.

A person skilled in the art will find instructions for identifying DNA sequences by means of hybridization inter alia in the handbook "The DIG System Users Guide for Filter Hybridization" from Boehringer Mannheim GmbH (Mannheim, Germany, 1993) and in Liebl et al. (International Journal of Systematic Bacteriology (1991) 41: 255–260). Hybridization takes place under stringent conditions, that is to say only hybrids in which the probe and target sequence, i.e. the polynucleotides treated with the probe, are at least 70% identical are formed. It is known that the stringency of the hybridization, including the washing steps, is influenced or determined by varying the buffer composition, the temperature, and the salt concentration. For reasons explained infra, the hybridization reaction is preferably preferably under a relatively low stringency compared with the washing steps (Hybaid Hybridisation Guide, Hybaid Limited, Teddington, UK, 1996).

A 5×SSC buffer at a temperature of approx. 50–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and subsequently 0.5×SSC (The DIG System User's Guide for Filter Hybridisation, Boehringer Marnheim, Mannheim, Germany, 1995) with a temperature of approximately 50–68° C. being established. It is optionally possible to lower the salt concentration to 0.1×SSC. Polynucleotide fragments which are, for example, at least 70% or at least 80% or at least 90% to 95% identical to the sequence of the probe employed can be isolated by increasing the hybridization temperature stepwise in approximately 1–2° C. increments. Commercial kits containing further instructions on hybridization are readily obtainable (e.g. DIG Easy Hyb from Roche Diagnostics GmbH, Mannheim, Germany, Catalogue No. 1603558).

A person skilled in the art will find instructions for amplification of DNA sequences with the aid of the polymerase chain reaction (PCR) inter alia in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994).

During work on the present invention it was found that Coryneform bacteria produce amino acids, in particular L-lysine, in an improved manner after over-expression of the oxyR gene.

To achieve an over-expression, the number of copies of the corresponding genes may be increased, or the promoter and regulation region, or the ribosome binding site upstream of the structural gene can be mutated. Expression cassettes that are incorporated upstream of the structural gene may also facilitate over-expression. Utilization of inducible promoters may also increase the expression of a desired gene in the course of production of L-lysine by fermentation. The expression is also improved by measures that prolong the life of the m-RNA. Furthermore, preventing the degradation of the enzyme may also increase the enzyme's activity. The genes or gene constructs can either be present in plasmids with a varying number of copies, or can be integrated and amplified in the chromosome. Alternatively, changing the composition of the media and the culture procedure may lead to over-expression of the desired gene.

A person skilled in the art will find instructions in this context inter alia in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European Patent Specification 0 472 869, in U.S. Pat. No. 4,601,893, in Schwarzer and Pühler (Bio/Technology 9, 84–87 (1991)), in Reinscheid et al. (Applied and Environmental Microbiology 60, 126–132 (1994)), in LaBarre et al. (Journal of Bacteriology 175, 1001–1007 (1993)), in Patent Application WO 96/15246, in Malumbres et al. (Gene 134, 15–24 (1993)), in Japanese Laid-Open Specification JP-A-10–229891, in Jensen and Hammer (Biotechnology and Bioengineering 58, 191–195 (1998)), in Makrides (Microbiological Reviews 60:512–538 (1996)) and in known textbooks of genetics and molecular biology.

By way of example, over-expression of the oxyR gene according to this invention was achieved with the aid of episomal plasmids. Suitable plasmids are those that are replicated in Coryneform bacteria. Numerous known plasmid vectors, such as pZ1 (Menkel et al., Applied and Environmental Microbiology (1989) 64: 549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other suitable plasmid vectors include those based on pCG4 (U.S. Pat. No. 4,489,160) or pNG2 (Serwold-Davis et al., FEMS Microbiology Letters 66, 119–124 (1990)) or pAG1 (U.S. Pat. No. 5,158,891).

An example of an oxyR over-expression plasmid is the E. coli-C. glutamicum shuttle vector pT-oxyRexp (FIG. 2). This vector contains the replication region rep of the plasmid pGA1 including the replication effector per (U.S. Pat. No. 5,175,108; Nesvera et al., Journal of Bacteriology 179, 1525–1532 (1997)), the tetracycline resistance-imparting tetA(Z) gene of the plasmid pAG1 (U.S. Pat. No. 5,158,891; gene library entry at the National Center for Biotechnology Information (NCBI, Bethesda, Md., USA) with accession number AF121000, the replication origin oriV of the plasmid pMB1 (Sutcliffe, Cold Spring Harbor Symposium on Quantitative Biology 43, 77–90 (1979)), the lacZα gene fragment including the lac promoter and a "multiple cloning site" (mcs) (Norrander, J. M. et al. Gene 26, 101–106 (1983)) and the mob region of the plasmid RP4 (Simon et al.,(1983) Bio/Technology 1:784–791).

Also suitable to achieve over-expression of the oxyR gene are plasmid vectors that are integrated into the chromosome, as has been described for duplication or amplification of the hom-thrB operon by Reinscheid et al. (Applied and Environmental Microbiology 60, 126–132 (1994)). In this method, the complete gene is cloned into a plasmid vector that can replicate in a host (typically E. coli), but not in C. glutamicum. Suitable vectors are, for example, pSUP301 (Simon et al., Bio/Technology 1, 784–791 (1983)), pK18mob or pK19mob (Schäfer et al., Gene 145, 69–73 (1994)), pGEM-T (Promega Corporation, Madison, Wis., USA), pCR2.1-TOPO (Shuman (1994). Journal of Biological Chemistry 269:32678–84; U.S. Pat. No. 5,487,993), pCR® Blunt (Invitrogen, Groningen, Holland; Bernard et al., Journal of Molecular Biology, 234: 534–541 (1993)), pEM1 (Schrumpf et al, 1991, Journal of Bacteriology 173:4510–4516) or pBGS8 (Spratt et al.,1986, Gene 41: 337–342). The plasmid vector containing the gene to be amplified is then transferred into the desired strain of C. glutamicum by conjugation or transformation. The method of conjugation is described, for example, by Schäfer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross-over" event, the resulting strain contains at least two copies of the gene in question.

In addition, it may be advantageous for the production of L-amino acids, in particular L-lysine, to enhance one or more enzymes of the particular biosynthesis pathway, of glycolysis, of anaplerosis, of the pentose phosphate cycle, of the citric acid cycle or of amino acid export and optionally regulatory proteins, in addition to the oxyR gene.

Thus, for example, for the preparation of amino acids, in particular L-lysine, one or more genes chosen from the group consisting of the dapA gene which codes for dihydrodipicolinate synthase (EP-B 0 197 335), the gap gene which codes for glyceraldehyde 3-phosphate dehydrogenase (Eikmanns (1992). Journal of Bacteriology 174:6076–6086), the tpi gene which codes for triose phosphate isomerase (Eikmanns (1992). Journal of Bacteriology 174:6076–6086), the pgk gene which codes for 3-phosphoglycerate kinase (Eikmanns (1992). Journal of Bacteriology 174:6076–6086), the pyc gene which codes for pyruvate carboxylase (Peters-Wendisch et al.(Microbiology 144, 915–927 (1998)), the lysC gene which codes for a feed back resistant aspartate kinase (EP-B-0387527; EP-A-0699759; WO 00/63388)

the lysE gene which codes for lysine export (DE-A-195 48 222)

the mqo gene which codes for malate-quinone oxidoreductase (Molenaar et al. (1998), European Journal of Biochemistry 254: 395–403), the zwf gene which codes for glucose 6-phosphate dehydrogenase (JP-A-09224661), the gnd gene which codes for 6-phosphogluconate dehydrogenase (U.S. Ser. No. 09/531,265), the sod gene which codes for superoxide dismutase (U.S. Pat. No. 6,569,650), the zwa1 gene which codes for the Zwa1 protein (DE: 199 59 328.0, DSM 13115) may be enhanced, in particular over-expressed, concomitant with oxyR gene over-expression.

It may also be advantageous for the production of amino acids, in particular L-lysine, in addition to the enhancement of the oxyR gene, at the same time to attenuate one or more genes chosen from the group the pek gene which codes for phosphoenol pyruvate carboxykinase (DE: 199 50,409.1, DSM 13047), the pgi gene which codes for glucose 6-phosphate isomerase U.S. Pat. No. 6,586,214, DSM 12969), the poxB gene which codes for pyruvate oxidase (DE: 199 51,975.7, DSM 13114), the zwa2 gene which codes for the Zwa2 protein (DE: 199 59,327.2, DSM 13113)

The term "attenuation" in this connection describes the reduction or exclusion of the intracellular activity of one or more enzymes proteins) in a microorganism that are coded by the corresponding DNA, by, for example using a weak promoter or using a gene or allele which codes for a corresponding enzyme with a low activity or by inactivating the corresponding gene or enzyme (protein), and optionally combining those measures.

It may also be advantageous for the production of amino acids, in particular L-lysine, in addition to over-expression of the oxyR gene, at the same time to eliminate undesirable side reactions, (Nakayama: "Breeding of Amino Acid Producing Micro-organisms", in: Overproduction of Microbial Products, Krumphanzl, Sikyta, Vanek (eds.), Academic Press, London, UK, 1982).

The microorganisms prepared according to the invention, for the purpose of production of L-amino acids, in particular L-lysine, can be cultured by batch process (continuous or discontinuous), fed batch, or repeated fed batch process. A summary of known culture methods is described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

A suitable culture medium must be used to meet the requirements of the particular strains. Descriptions of culture media for various microorganisms are contained in the handbook "Manual of Methods for General Bacteriology" of the American Society for Bacteriology (Washington D.C., USA, 1981).

Sugars and carbohydrates (e.g., glucose, sucrose, lactose, fructose, maltose, molasses, starch and cellulose), oils and fats (e.g., soya oil, sunflower oil, groundnut oil and coconut fat), fatty acids (e.g., palmitic acid, stearic acid and linoleic acid), alcohols (e.g., glycerol and ethanol), and organic acids (e.g., acetic acid) may be used as the carbon source. These substance may be used individually or as a mixture.

Organic nitrogen-containing compounds (e.g., peptones, yeast extract, meat extract, malt extract, corn steep liquor, soya bean flour and urea) or inorganic compounds (e.g., ammonium sulfate, ammonium chloride, ammonium phosphate, ammonium carbonate and ammonium nitrate) may be used as the nitrogen source. The sources of nitrogen may be used individually or as a mixture.

The phosphorus source may be phosphoric acid, potassium dihydrogen phosphate, or dipotassium hydrogen phosphate (or the corresponding sodium-containing salts). Furthermore, the culture medium must contain salts of metals (e.g., magnesium sulfate or iron sulfate) that are necessary for growth. Finally, essential growth substances, such as amino acids and vitamins, may be used in addition to the above-mentioned substances. Moreover, suitable precursors may be added to the culture medium. The starting substances mentioned may be added to the culture in the form of a single batch, or may be added in a suitable manner during fermentation.

Basic compounds (e.g., sodium hydroxide, potassium hydroxide, ammonia or aqueous ammonia) or acidic compounds (e.g., phosphoric acid or sulfuric acid) may be added in a suitable manner to control the pH. Fatty acid polyglycol esters may be used to control the development of foam. In order to maintain the stability of plasmids, suitable substances having a selective action, such as antibiotics, may be added to the medium. In order to maintain aerobic conditions, oxygen or oxygen-containing gas mixtures, such as air, may be introduced into the culture. The temperature of the culture is normally 20° C. to 45° C., and preferably 25° C. to 40° C. Fermentation is continued until the maximum of the desired product has formed. This objective is normally reached within 10 hours to 160 hours.

Methods for the determination of L-amino acids are known from the prior art. The analysis may thus be carried out, for example, by ion exchange chromatography with subsequent ninhydrin derivation as described by Spackman et al. (Analytical Chemistry, 30, (1958), 1190) or by reversed phase HPLC as described by Lindroth et al. (Analytical Chemistry (1979) 51: 1167–1174).

The process according to the invention is used for the production of amino acids, in particular L-lysine, by fermentation.

The isolation of plasmid DNA from *Escherichia coli* and all techniques of restriction, Klenow and alkaline phosphatase treatment were performed as described in Sambrook et al. (Molecular Cloning. A Laboratory Manual (1989) Cold Spring Harbor Laboratory Press, Cold Spring Harbor, N.Y., USA). Methods for transformation of *Escherichia coli* and the composition of the usual nutrient media, such as LB or TY medium, are also described in this handbook.

The following microorganisms were deposited at the Deutsche Sanunlung für Mikroorganismen und Zellkulturen (DSMZ=German Collection of Microorganisms and Cell Cultures, *Mascheroder Weg* 1b D-38124 Braunschweig, Germany) in accordance with the Budapest Treaty:

*Corynebacterium glutamicum* DSM5715/pT-oxyRexp which was deposited on Apr. 4, 2000 as DSM 13457, and

*Escherichia coli* DH5α/pEC-T18mob2 which was deposited on Jan. 1, 2000 as DSM 13244.

Having generally described this invention, a further understanding can be obtained by reference to certain specific examples, which are provided herein for purposes of illustration only, and are not intended to be limiting unless otherwise specified.

EXAMPLES

Example 1

Preparation of a Genomic Cosmid Gene Library from *Corynebacterium glutamicum* ATCC 13032

Chromosomal DNA from *Corynebacterium glutamicum* ATCC 13032 was isolated as described by Tauch et al.

(1995, Plasmid 33:168–179) and partly cleaved with the restriction enzyme Sau3AI (Amersham Pharmacia, Freiburg, Germany, Product Description Sau3AI, Code no. 27–0913–02). The DNA fragments were dephosphorylated with shrimp alkaline phosphatase (Roche Diagnostics GmbH, Mannheim, Germany, Product Description SAP, Code no. 1758250). The DNA of the cosmid vector Super-Cos1 (Wahl et al. (1987) Proceedings of the National Academy of Sciences USA 84:2160–2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27–0948–02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA so treated was mixed with the treated ATCC13032 DNA and the batch was treated with T4 DNA ligase (Amersham Pharmacia, Freiburg, Germany, Product Description T4-DNA-Ligase, Code no. 27-0870-04). The ligation mixture was then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Research 16:1563–1575) the cells were taken up in 10 mM $MgSO_4$ and mixed with an aliquot of the phage suspension. The infection and titering of the cosmid library were carried out as described by Sambrook et al. (1989, Molecular Cloning: A laboratory Manual, Cold Spring Harbor), the cells being plated out on LB agar (Lennox, 1955, Virology, 1:190) with 100 mg/l ampicillin. After incubation overnight at 37° C., recombinant individual clones were selected.

Example 2

Isolation and Sequencing of the oxyR Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Diagnostics GmbH, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, Holland, Product Description Zero Background Cloning Kit, Product No. K2500-01), was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343–7) into the *E. coli* strain DH5αMCR (Grant, 1990, Proceedings of the National Academy of Sciences U.S.A., 87:4645–4649) and plated out on LB agar (Lennox, 1955, Virology, 1:190) with 50 mg/l zeocin.

Plasmid preparation of the recombinant clones was carried out with Biorobot 9600 (Product No. 900200, Qiagen, Hilden, Germany). DNA sequencing was administered by the dideoxy chain termination method of Sanger et al. (1977, Proceedings of the National Academy of Sciences U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. Separation by gel electrophoresis and analysis of the sequencing reaction were carried out in a "Rotiphoresis NF Acrylamide/Bisacrylamide" Gel (29: 1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pZero1 derivatives were assembled to a continuous contig. The computer-assisted coding region analysis was prepared with the XNIP program (Staden, 1986, Nucleic Acids Research, 14:217–231). Further analyses were carried out with the "BLAST search program" (Altschul et al., 1997, Nucleic Acids Research, 25:3389–3402) against the non-redundant databank of the "National Center for Biotechnology Information" (NCBI, Bethesda, Md., USA).

The resulting nucleotide sequence is shown in SEQ ID No. 1. Analysis of the nucleotide sequence revealed an open reading frame of 981 base pairs, which was designated the oxyR gene. The oxyR gene codes for a protein of 327 amino acids.

Example 3

Preparation of a Shuttle Vector pT-oxyRexp for Enhancement of the OxyR Gene in *C. glutamicum*

<3.1> Cloning of the oxyR Gene

From the *C. glutamicum* ATCC strain 13032, chromosomal DNA was isolated by the method of Eikmanns et al. (Microbiology 140: 1817–1828 (1994)). On the basis of the sequence of the oxyR gene known for *C. glutamicum* from Example 2, the following oligonucleotides were chosen for the polymerase chain reaction.

```
OxyR (oxy-exp; SEQ ID No.3):
5'GAT CGA GAA TTC AAA GGA AGA TCA GCT TAG 3'

OxyR (oxy R2; SEQ ID No.4):
5'GGA AAA CCT CTA GAA AAA CT 3'
```

The primers shown were synthesized by ARK Scientific GmbH Biosystems (Darmstadt, Germany) and the PCR reaction was carried out by the standard PCR method of Innis et al. (PCR protocols. A guide to methods and applications, 1990, Academic Press) with Pwo-Polymerase from Roche Diagnostics GmbH (Mannheim, Germany). With the aid of the polymerase chain reaction, a 1.43 kbp DNA fragment containing the oxyR gene was isolated. Furthermore, the OxyR (oxy-exp) primer contains the EcoRI restriction endonuclease cleavage site sequence and the OxyR (oxy R2) contains the XbaI restriction endonuclease cleavage site sequence, underlined in the corresponding nucleotide sequence above.

The approximately 1.43 kb DNA fragment containing the oxyR gene was ligated into the pCR® Blunt II vector (Bernard et al., Journal of Molecular Biology, 234: 534–541 (1993)) using the Zero Blunt™ Kit of Invitrogen Corporation (Carlsbad, Calif., USA; Catalogue Number K2700-20) and subsequently transformed into the E. coli strain Top10 (Grant et al., Proceedings of the National Academy of Sciences USA, 87 (1990) 4645–4649) according to the manufacturer's instructions (Invitrogen Corporation, Carlsbad, Calif., USA). Plasmid-carrying cells were selected by plating out the transformation batch on LB agar (Sambrook et al., Molecular cloning: A Laboratory Manual. $2^{nd}$ Ed. Cold Spring Harbor Laboratory Press, Cold Spring Harbor, N.Y., 1989), which had been supplemented with 25 mg/l kanamycin. Plasmid DNA was isolated from a transformant with the aid of the QIAprep Spin Miniprep Kit from Qiagen (Hilden, Germany) and checked by treatment with the restriction enzyme XbaI and EcoRI with subsequent agarose gel electrophoresis (0.8%). The DNA sequence of the amplified DNA fragment was verified by DNA sequencing. Accordingly, the plasmid was called pCR-oxyRexp. The strain was called E. coli Top10/pCR-oxyRexp.

<3.2> Preparation of the E. coli-C. glutamicum Shuttle Vector pEC-T18mob2

The E. coli-C. glutamicum shuttle vector was constructed according to the prior art.

The vector contains the replication region rep of the plasmid pGA1 including the replication effector per (U.S. Pat. No. 5,175,108; Nesvera et al., Journal of Bacteriology 179, 1525–1532 (1997)), the tetracycline resistance-imparting tetA(Z) gene of the plasmid pAG1 (U.S. Pat. No. 5,158,891; gene library entry at the National Center for Biotechnology Information (NCBI, Bethesda, Md., USA) with the accession number AF121000), the replication region oriV of the plasmid pMB1 (Sutcliffe, Cold Spring Harbor Symposium on Quantitative Biology 43, 77–90 (1979)), the lacZα gene fragment including the lac promoter and a multiple cloning site (mcs) (Norrander, J. M. et al. Gene 26, 101–106 (1983)) and the mob region of the plasmid RP4 (Simon et al.,(1983) Bio/Technology 1:784–791). The vector constructed was transformed in the E. coli strain DH5α (Hanahan, In: DNA cloning. A Practical Approach. Vol. I IRL-Press, Oxford, Washington D.C., USA). Selection of plasmid-carrying cells was carried out by plating out the transformation batch on LB agar (Sambrook et al., Molecular cloning: a laboratory manual. $2^{nd}$ Ed. Cold Spring Harbor Laboratory Press, Cold Spring Harbor, N.Y.), which had been supplemented with 5 mg/l tetracycline. Plasmid DNA was isolated from a transformant with the aid of the QIAprep Spin Miniprep Kit from Qiagen and checked by restriction with the restriction enzyme EcoRI and HindIII and subsequent agarose gel electrophoresis (0.8%). The plasmid was called pEC-T18mob2 and is shown in FIG. 1.

<3.3> Cloning of oxyR into the E. coli-C. glutamicum Shuttle Vector pEC-T18mob2

The E. coli-C. glutamicum shuttle vector pEC-T18mob2 described in Example 3.2 was used as the vector. DNA of this plasmid was cleaved completely with the restriction enzymes EcoRI and XbaI and then dephosphorylated with shrimp alkaline phosphatase (Roche Diagnostics GmbH, Mannheim, Germany, Product Description SAP, Product No. 1758250).

The oxyR gene was isolated from the plasmid pCR-oxyRexp described in Example 3.1 by complete cleavage with the enzymes EcoRI and XbaI. The approximately 1.43 kbp DNA fragment containing the oxyR gene was isolated from the agarose gel with the QiaExII Gel Extraction Kit (Product No. 20021, Qiagen, Hilden, Germany).

The oxyR fragment obtained in this manner was mixed with the prepared vector pEC-T18mob2 and the batch was treated with T4 DNA ligase (Amersham Pharmacia, Freiburg, Germany, Product Description T4-DNA-Ligase, Code no. 27-0870-04). The ligation batch was transformed into the E. coli strain DH5α (Hanahan, In: DNA cloning. A Practical Approach. Vol. I. IRL-Press, Oxford, Washington D.C., USA). Selection of plasmid-carrying cells was made by plating out the transformation batch on LB agar (Lennox, 1955, Virology, 1:190) with 5 mg/l tetracycline. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and cleaved with the restriction enzymes EcoRI and XbaI to check the plasmid by subsequent agarose gel electrophoresis. The resulting plasmid was called pT-oxyRexp. It is shown in FIG. 2.

Example 4

Transformation of the Strain DSM5715 with the Plasmid pT-oxyRexp

The strain DSM5715 was transformed with the plasmid pT-oxyRexp using the electroporation method described by Liebl et al., (FEMS Microbiology Letters, 53:299–303 (1989)). Selection of the transformants took place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which had been supplemented with 5 mg/l tetracycline. Incubation was carried out for 2 days at 33° C.

Plasmid DNA was isolated from a transformant by conventional methods (Peters-Wendisch et al., 1998, Microbiology, 144, 915–927), cleaved with the restriction endonucleases EcoRI and XbaI, and the plasmid was checked by subsequent agarose gel electrophoresis. The resulting strain was called DSM5715/pT-oxyRexp.

Example 5

Preparation of L-lysine

The C. glutamicum strain DSM5715/pT-oxyRexp obtained in Example 4 was cultured in a nutrient medium suitable for the production of L-lysine by fermentation, and the L-lysine content in the culture supernatant was determined.

To that end, the strain was first incubated on an agar plate with the corresponding antibiotic (brain-heart agar with tetracycline (5 mg/l)) for 24 hours at 33° C. A pre-culture was inoculated (10 ml medium in a 100 ml conical flask). The complete CgIII medium was used as the medium for the pre-culture starting from this agar plate culture.

| Cg III Medium | |
| --- | --- |
| NaCl | 2.5 g/l |
| Bacto-Peptone | 10 g/l |
| Bacto-Yeast extract | 10 g/l |
| Glucose (autoclaved separately) | 2% (w/v) |
| The pH was brought to pH 7.4 | |

Tetracycline (5 mg/l) was added to the pre-culture medium. The pre-culture was incubated for 16 hours at 33°

C. at 240 rpm on a shaker. A main culture was inoculated from this pre-culture such that the initial OD (660 nm) of the main culture was 0.05. MM medium was used for the main culture.

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| L-Leucine (sterile-filtered) | 0.1 g/l |
| $CaCO_3$ | 25 g/l |

The CSL, MOPS, and the salt solution were brought to pH 7 with aqueous ammonia and autoclaved. The sterile substrate and vitamin solutions were then added, as well as the dry, autoclaved $CaCO_3$.

Cell-growth was performed in a 10 ml volume in a 100 ml conical flask with baffles. Tetracycline (5 mg/l) was added. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of L-lysine formed was determined with an amino acid analyzer from Eppendorf-BioTronik (Hamburg, Germany) by ion exchange chromatography and post-column derivation with ninhydrin detection.

The result of the experiment is shown in table 1.

TABLE 1

| Strain | OD (660 nm) | Lysine HCl (g/l) |
|---|---|---|
| DSM5715 | 6.8 | 13.68 |
| DSM5715/pT-oxyRexp | 6.5 | 14.73 |

Obviously, numerous modifications and variations on the present invention are possible in light of the above teachings. It is therefore to be understood that within the scope of the appended claims, the invention may be practiced otherwise than as specifically described herein.

What is claimed is:

1. An isolated polynucleotide which encodes a protein comprising the amino acid sequence of SEQ ID NO: 2.

2. The isolated polynucleotide of claim 1 which comprises SEQ ID NO: 1.

3. A vector comprising the isolated polynucleotide of claim 1.

4. A host cell comprising the isolated polynucleotide of claim 1.

5. The host cell of claim 4, which is a *Corynebacterium*.

6. The host cell of claim 4, wherein said host cell is selected from the group consisting of *Corynebacterium glutamicum, Corynebacterium acetoglutamicum, Corynebacterium acetoacidophilum, Corynebacterium melassecola, Corynebacterium thermoaminogenes,* and *Brevibacterium flavum*.

7. A modified *Corynebacterium* comprising multiple copies of the polynucleotide of claim 1.

8. A method for making an OxyR transcriptional regulator protein, comprising:

a) culturing the host cell of claim 4 for a duration of time under conditions suitable for expression of an OxyR transcriptional regulator protein; and b) collecting the OxyR transcriptional regulator protein.

9. An isolated polynucleotide which comprises nucleotides 491 to 1471 of SEQ ID NO: 1.

10. An isolated polynucleotide, which is fully complementary to nucleotides 491 to 1471 of SEQ ID NO: 1.

11. A vector comprising the isolated polynucleotide of claim 9.

12. A host cell comprising the isolated polynucleotide of claim 9.

13. The host cell of claim 12, which is a *Corynebacterium*.

14. The host cell of claim 12, wherein said host cell is selected from the group consisting of *Corynebacterium glutamicum, Corynebacterium acetoglutamicum, Corynebacterium acetoacidophilum, Corynebacterium melassecola, Corynebacterium thermoaminogenes,* and *Brevibacterium flavum*.

15. A modified *Corynebacterium* comprising multiple copies of the polynucleotide of claim 9.

16. A method for making an OxyR transcriptional regulator protein, comprising:

a) culturing the host cell of claim 12 for a duration time under conditions suitable for expression of an OxyR transcriptional regulator protein; and b) collecting the OxyR transcriptional regulator protein.

17. A *Corynebacterium* modified to contain a polynucleotide encoding SEQ ID NO:2 under the control of an exogenous promoter or expression cassette, wherein the expression of the gene product of said polynucleotide is increased relative to a corresponding, unmodified *Corynebacterium*.

18. A method for making an L-amino acid comprising:

culturing in a suitable medium a cell comprising a polynucleotide encoding SEQ ID NO:2, and recovering the L-amino acid, wherein said cell overexpresses said polynucleotide and wherein said overexpression is achieved by increasing the copy number of said polynucleotide or operably linking to said polynucleotide a promoter or expression cassette to increase the expression of said polynucleotide.

19. The method of claim 18, wherein said L-amino acid is L-lysine.

20. The method of claim 18, wherein said cell is a *Corynebacterium*.

21. The method of claim 18, wherein said cell is selected from the group consisting of *Corynebacterium glutamicum, Corynebacterium acetoglutamicum, Corynebacterium acetoacidophilum, Corynebacterium melassecola, Corynebacterium thermoaminogenes,* and *Brevibacterium flavum*.

22. *Corynebacterium glutamicum* DSM 13457.

* * * * *